United States Patent
Ten Bruggenkate

(10) Patent No.: US 8,496,478 B2
(45) Date of Patent: Jul. 30, 2013

(54) INTRA-OSSEOUS IMPLANT

(75) Inventor: Christiaan Michiel Ten Bruggenkate, Loevestein (NL)

(73) Assignee: Ten Bruggenkate Kaakchirugie B.V. (NL)

( * ) Notice: Subject to any disclaimer, the term of this patent is extended or adjusted under 35 U.S.C. 154(b) by 1223 days.

(21) Appl. No.: 10/562,387

(22) PCT Filed: Jun. 28, 2004

(86) PCT No.: PCT/EP2004/007058
§ 371 (c)(1),
(2), (4) Date: May 11, 2006

(87) PCT Pub. No.: WO2005/002462
PCT Pub. Date: Jan. 13, 2005

(65) Prior Publication Data
US 2008/0064010 A1 Mar. 13, 2008

(30) Foreign Application Priority Data
Jun. 30, 2003 (EP) .................................. 03077039

(51) Int. Cl.
*A61C 8/00* (2006.01)
(52) U.S. Cl.
USPC ........................................................ 433/174
(58) Field of Classification Search
USPC ................... 433/172–176, 201.1, 202.1, 215, 433/220, 221
See application file for complete search history.

(56) References Cited

U.S. PATENT DOCUMENTS

| 4,468,200 | A | * | 8/1984 | Munch | 433/174 |
| 4,722,688 | A | * | 2/1988 | Lonca | 433/173 |
| 5,302,126 | A | | 4/1994 | Wimmer et al. | |
| 5,759,034 | A | * | 6/1998 | Daftary | 433/173 |
| 5,921,774 | A | * | 7/1999 | Kanomi et al. | 433/173 |
| 5,954,504 | A | * | 9/1999 | Misch et al. | 433/174 |
| 6,039,568 | A | | 3/2000 | Hinds | |
| 6,099,312 | A | * | 8/2000 | Alvaro | 433/174 |
| 2002/0055783 | A1 | | 5/2002 | Tallarida et al. | |
| 2002/0102518 | A1 | * | 8/2002 | Mena | 433/174 |
| 2004/0096804 | A1 | * | 5/2004 | Vogt et al. | 433/173 |
| 2004/0146834 | A1 | | 7/2004 | Haessler | |

FOREIGN PATENT DOCUMENTS

| DE | 102 04 324 A1 | 8/2002 |
| EP | 0 922 439 A2 | 6/1999 |
| EP | 0 974 311 A1 | 1/2000 |

* cited by examiner

*Primary Examiner* — Heidi M Eide
(74) *Attorney, Agent, or Firm* — Wood, Phillips, Katz, Clark & Mortimer

(57) ABSTRACT

The invention relates to an intra-osseous implant for placement in bone of a human or animal body, which allows an accurate implant position at a desired depth into bone tissue, providing without losing a high degree of primary implant stability, including at least one intra-osseous part intended for placement in the bone tissue having an apical side and a cervical side, which part is provided on its circumferential surface with a thread running in the direction of the apical end and with one or more grooves extending in longitudinal direction and interrupting the screw thread into multiple interrupted screw thread parts serving as retention elements allowing the placement of the implant in longitudinal direction into the bone tissue but preventing the removal of the implant in opposite longitudinal direction of the bone and a support part present at the cervical side of the at least one intra-osseous part intended for supporting a prosthetic element.

4 Claims, 12 Drawing Sheets

INTRA-OSSEOUS IMPLANT

Figure 1A:
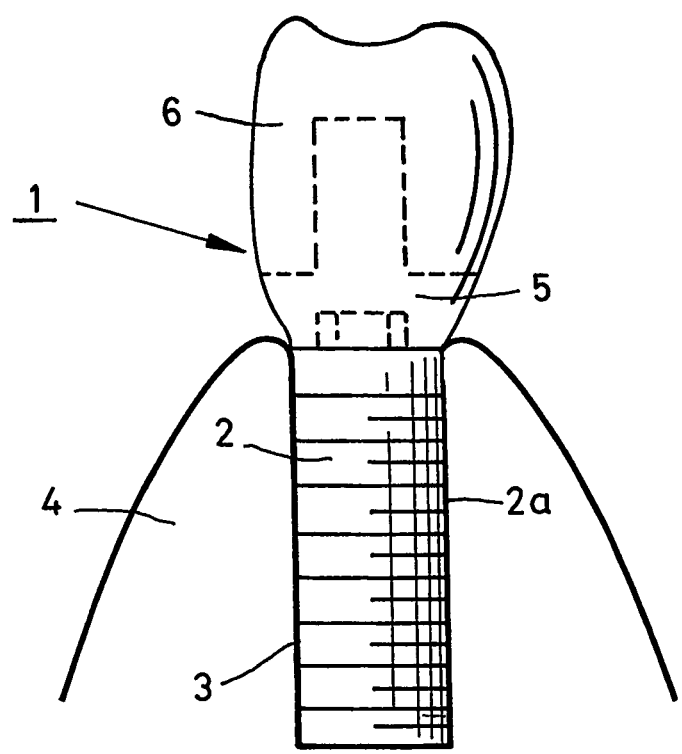

The invention relates to an intra-osseous implant for placement in bone of a human or animal body comprising at least
one intra-osseous part intended for placement in said bone tissue having an apical side and a cervical side and composed of a body friendly material, which part is provided on its circumferential surface with a thread running in the direction of the apical end; and
a support part present at said cervical side of said at least one intra-osseous part intended for supporting a prosthetic element.

Present intra-osseous implants are frequently used for medical purposes, such as (hip-, knee- and finger-) joint prostheses and bone screws for traumatology. Also these intra-osseous implants are used as dental implants in dentistry and oral and maxillofacial surgery.

An important development in dentistry and oral and maxillofacial surgery in the last two decades, is the application of dental implants. These 'artificial' tooth roots are used to replace lost natural teeth and genitally absent teeth. Upon these implants removable overdentures or fixed crowns or bridges can be placed.

Dental implants can be placed in the bone after implant bed preparation with one or more drills. After a certain integration period they can be loaded, for example by chewing. The prosthetic parts will provide the patients with essential functions like chewing ability, speech, appearance and self-esteem.

Most dental implants are rotation symmetric, the majority having a screw thread design.

Usually the threaded dental implants excludes an asymmetric implant design (e.g. angled or bevelled or scalloped), since the critical position of the implant clashes with the intended implant placement depth. Although the screw thread provides the implant of a good retention, it limits on the other hand the depth accuracy of the placed implant.

The pitch of the screw thread defines the depth positioning of an implant. A large pitch allows a quick insertion procedure, but the depth positioning towards the surrounding bone and the next structures is less accurate. On the other hand a screw thread having a small pitch allows an accurate implant position, but offers less primary implant stability and a time consuming surgical procedure.

Rotation asymmetric implants benefit in this respect from a cylinder design, since the implant is tapped or pushed into its desired position, after the implant bed is prepared the appropriate drills. This is a very fast surgical procedure. However the retention of the implant towards the surrounding bone is limited, especially if the bone is of a non-dense (weak or loose) structure.

In other words the cylindrical implants have a better position ability than screw implants, but the primary stability is lower. This observation is not only applicable for implant dentistry, but also for medical indications.

With respect to the above mentioned, the invention aims to provide a medical intra-osseous implant and especially a dental intra-osseous implant, which allows an accurate implant position at a desired depth into bone tissue, providing without losing a high degree of primary implant stability. Also the proposed implant design will allow a short surgical procedure with an improved suture of bone tissue to the implant as well as providing an intra-osseous implant having a strong anti-rotation characteristic.

According to the invention the intra-osseous implant is characterized in that the intra-osseous part is provided with one or more grooves extending in longitudinal direction and interrupting the screw thread into multiple interrupted screw thread parts, said multiple interrupted screw thread parts serving as retention elements allowing the placement of the implant in longitudinal direction into said bone tissue but preventing the removal of the implant in opposite longitudinal direction out of said bone.

The presence of one or more groove-like interruptions of the screw thread allows a quick and accurate placement of the implant into the bone, without the necessity to screw the implant into its proper position. The implant can merely be tapped or pushed into its proper position significantly reducing the time of the surgical procedure.

The remaining thread parts on the intra-osseous implant surface function as retention elements (like shark teeth) exerting vertical and rotational retention forces on the surrounding bone tissue. This ensures a proper primary implant stability of the intra-osseous implant according to the invention.

However the remaining thread parts (retention elements) still form a (though interrupted) screw thread, so that the implant can also be (re)positioned by means of screw (rotation) action. The interrupted screw thread also allows removal of an implant that has just been inserted, but intra-operatively regarded as not properly positioned.

The implant invention combines the advantages of a fast surgical procedure and an accurate placement and positioning of the intra-osseous implant. Also it provides the implant of a good primary stability and a high retention against vertical and rotational forces.

In a specific example of the invented implant the groove extends over the entire length of the intra-osseous part of the implant, wherein the depth of the groove can be smaller, equal or greater than the height of the screw thread.

More in particular the width of the groove varies in the direction of the apical side of said intra-osseous part and more in particular widens. Also the depth of the groove may vary in the direction of the apical side of said intra-osseous part and more in particular becomes larger, or the height of the screw thread may vary in the direction of the apical side of said intra-osseous part and more in particular becomes smaller.

In specific and favourable designs of medical or dental (or veterinary) bone implants according to the invention the intra-osseous part comprises multiple grooves.

A better stability of the implant according to the invention is acquired due to the longitudinal grooves, which are present in an equidistant manner in the surface of the intra-osseous part of the implant.

With an advantageous embodiment the insertion of the implant into the bone is facilitated and speed as according to the invention the intra-osseous part has a cylindrical cross section. However in other embodiment the intra-osseous part may have a near cylindrical cross section, for example a conical, elipsonal, oval cross section.

More in particular the intra-osseous part may exhibit a polygonal cross section, for example a pentagon or hexagonal or heptagon or octagonal cross section.

A further improved insertion of the implant according to the invention is obtained as the intra-osseous part becomes smaller in the apical direction.

In specific implant designs the intra-osseous part of the implant may have a conical shape or be narrower towards the apex of the implant.

In another embodiment the support part is positioned under an angle on said intra-osseous part with respect to the direction of implant.

In another specific design the intra-osseous implant is intended as a dental implant, where the shape is adapted to the shape of the alveolar crest. Unlike most dental implants available at present, the shoulder of the implant, that is the circumferential edge of the support (or connection) part will not be rotation symmetric. It may for example be scalloped, bevelled, curved or angled to accommodate the bony contours of the jawbone. In this manner the implant shape will allow proper aesthetics in the regions of aesthetic relevance (mainly the frontal teeth in the upper jaw).

The shape of the natural tooth is such that the crown on the buccal (lip- or cheek- or out-) side (and palatal or oral side), extends further to the apex (towards the end of the implant) than on the interproximal sides. In most dental implants the rotation symmetric design of the implant does not allow a crown margin that follows these contours. The result is that the crown is buccally not deep enough and interproximally too deep in to the tissues. The first aspect is negative for the aesthetic appearance (it is less beautiful, sometimes showing implant metal). The second may impair the hygienic possibilities and may lead to peri-implant bone loss.

The disadvantages of the above mentioned conventional dental implants can be dealt with by creating a bevel (concave excavation or flattening) on one side (meant to be placed on the buccal side of the jaw) of the implant. In this case the above-mentioned problems of a too deep placed implant shoulder (=crown margin) on the interproximal sides and a not deep enough placed implant shoulder (=crown margin) on the buccal side, can be dealt with.

The present dental implants are usually of a straight design. The shape of a natural tooth shows a small angle between the root and the crown of the tooth, in a specific embodiment the support part is positioned under an angle on said intra-osseous part with respect to the direction of implant. The implant invention allows the implant to be of an angled design, thus dealing with anatomical requirements of the jaws and teeth.

Figure 1B:
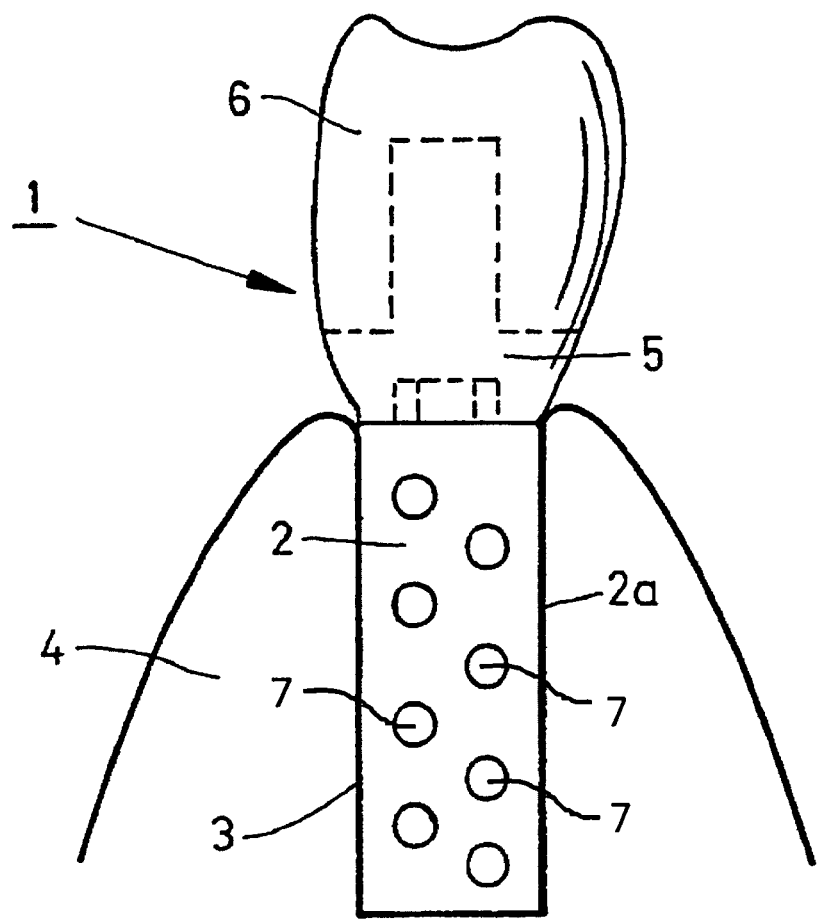
Figure 1C:
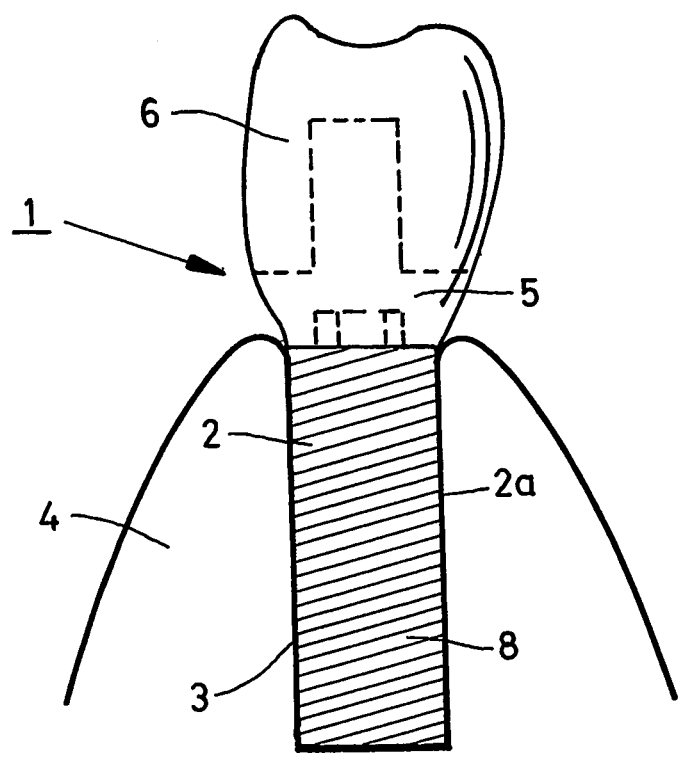
Figure 2:
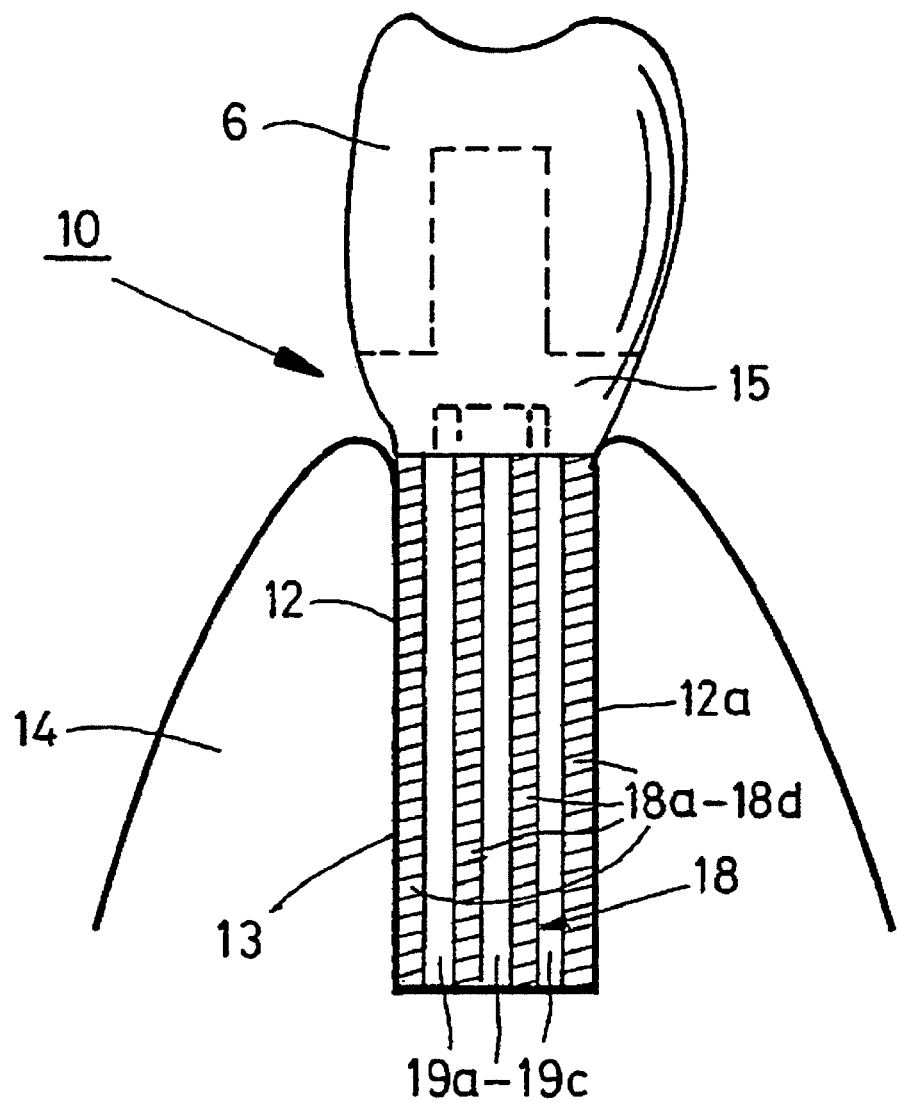

The invention will be described with reference to a drawing, which drawing shows in:

FIG. 1a-1c several embodiments of an intra-osseous implants according to the state of the art;

FIG. 2 a first embodiment of an intra-osseous implant according to the invention;

FIGS. 3-10 more embodiments of an intra-osseous implant according to the invention.

The following description of the Figures describe several embodiments of intra-osseous implant designs, which are meant to be used as dental implants. However the invention is, depending on the indication and medical application as well as the surgical treatment, not limited to only dental implant, but also applicable to other bone implants or bone screws or bone nails.

FIGS. 1a-1c disclose conventional dental implants 1 according to the state of the art having an elongated shape and manufactured of a tissue friendly material, such as titanium or a titanium alloy. The implant 1 has a root part also called an intra-osseous part 2, which is meant to be placed in an implant bed preparation 3 in the jaw bone 4.

The intra-osseous implant 1 also has a support connection or mounting part 5, which usually is utilised to insert the implant with. The support part 5 is also used to support and mount or connect the prosthetic device 6 (supra-structure, e.g. crown, bridge or over denture) at a later stage.

An essential factor in implant dentistry is the accurate depth of the intra-osseous implant 1 into the bone 4 during placement. An accurate depth in implant placement has a significant aesthetic relevance, but is also of importance for a good oral hygiene and peri-implant health. Disregarding the rules of the biologic width (in the event an implant is placed too deeply) will lead to bone loss. On the other hand, if the implant is not placed deeply enough, the aesthetic result will be disappointing (visible crown margin or implant shoulder).

An accurate placement of implants can be achieved by using cylindrical implants as shown in FIGS. 1a and 1b. Such cylindrical implants 1 allow a quick and accurate placement of the implant into the bone 4, but the cylindrically shaped intra-osseous part 2 provides a less primary stability in the implant bed preparation 3 than with a screw implant.

In order to increase the bone contact between the circumferential surface 2a of the intra-osseous part 2 and the bone tissue wall of the implant bed preparation 3 and therefore to improve the implant stability in the jaw bone 4, a well-known intra-osseous implant 1b has an intra-osseous part 2 with a hollow cylinder design provided with lateral perforations 7 to increase ingrowth of bone tissue.

Another well known implant design 1c shows an intra-osseous part 2 with a screw thread 8 provided in its circumferential surface 2a. The screw thread 8 provides the implant 1 with a high primary stability at implant placement. It also guarantees an increased implant-bone contact surface and allows the implant to be loaded (e.g. by chewing) at an earlier stage after the implant procedure.

A disadvantage of a screw thread 8 present in the circumferential surface 2a of the intra-osseous part 2 of the implant 1 is that the limited accuracy in depth positioning is limited even if the implant is not rotation symmetric (scalloped or bevelled or angled).

A screw thread 8 with a large pitch will permit a quick implant placement, but involves minor accuracy as to the depth positioning of the implant with respect to the surrounding bone tissue. A screw thread 8 with a smaller pitch allows a more accurate depth positioning, however such design requires in turn a more time consuming surgery procedure and in extreme cases less primary stability of the implant due to the smaller thread.

The invention aims to avoid above mentioned drawbacks and design an implant that allows a swift and accurate implant placement, providing a high degree of (primary) implant stability.

The intra-osseous implant 10 as shown in FIG. 2 according to the invention consists of an elongated intra-osseous part 12 of a tissue friendly material and a support or connection part 15 intended for implant insertion and acting as a support or mounting area for a prosthetic device 6 (a supra-structure, e.g. crown, bridge or over denture) at a later stage.

The intra-osseous part 12 of the implant 10 carries on its surface 12a a screw thread 18 with a certain pitch.

According to the invention, the intra-osseous part 12 as shown in FIG. 2 has on its circumferential surface 12a a screw thread 18, which thread 18 is interrupted by one or more longitudinal extending grooves 19a-19c. The presence of one or more grooves 19a-19c results in a screw thread 18, which is composed of several sections 18a-18d depending on the number of grooves 19a-19c.

More in particular these grooves 19a-19c etc. are present in an equidistant manner in the surface 12a of the intra-osseous part 12 of the implant 10. Furthermore the intra-osseous part 12 of the implant may preferably have a cylindrical cross-section. However also near cylindrical cross-sections, like an elliptical, oval or conical cross-section are possible.

More in particular the intra-osseous implant according to the invention may have a polygonal cross-section, for example a squar or pentagonal or hexagonal or heptagonal or octagonal cross-section.

Also combinations of one or more of the above embodiments are possible.

As a result of the configuration of the interrupted screw thread 18, the intra-osseous implant 10 according to the invention is not only a screw implant, but can also be used as a cylinder implant. The cylindrical ground form allows a swift surgical procedure, since the screw action is not necessary. After placement of the implant 10 at the desired position and depth into the bone 14, the screw parts 18a-18c etc. present on the circumferential surface 12a of the intra-osseous part 12 act as retention elements positioned side-by-side in a longitudinal manner.

These retention elements function like shark teeth hooking on to the bone tissue 13 surrounding the implanted intra-osseous part 12. With these retention elements the implant 10 will have a good primary stability and a high retention against vertical and rotational forces.

Due to the fact that the retention elements 18a-18c etc. are situated on adjacent rows orientated parallel to the implant axis, no undesired turning or rotation of the intra-osseous implant 10 during implant insertion into the implant preparation bed 13 will occur. Instead, the insertion of the implant 10 simply by pushing or tapping it into its desired place, will guarantee a proper orientation and position with respect to the surrounding (bone) tissue.

If so desired a symmetric or non-symmetric implant 10 can be properly (re)positioned in height (or depth) by turning the implant 10 in a screw motion. Although interrupted by the longitudinal grooves 19a-19c etc. the interrupted screw thread parts 18a-18c etc. still function as a complete thread with a certain pitch, thus allowing to alter the desired insertion depth and to maintain primary stability.

Figure 3B:
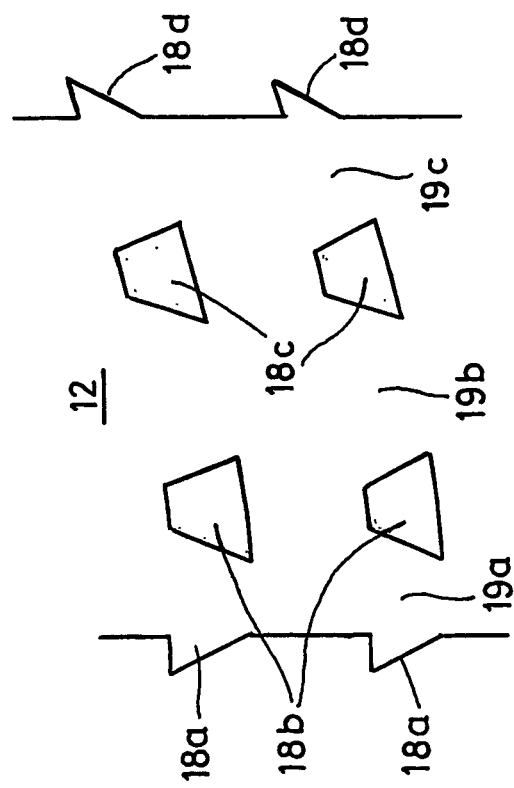
Figure 3A:
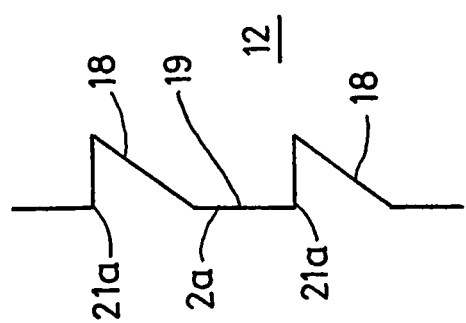

FIGS. 3a and 3b show detailed views of the embodiment shown in FIG. 2. The grooves 19a-19c etc. extend in longitudinal direction along the circumferential surface 12a of the intra-osseous part 12, in such a manner that the grooves 19a-19c more or less flatten the extending edge 21a-21c etc. of the thread 18a-18c etc.

Each extended edge 21a-21c etc. of the thread 18 functions as a retention element towards the bone tissue 14 surrounding the intra-osseous part 12. A possibly wrongly inserted implant 10 can be removed using the interrupted screw thread 18a-18c etc., by simply unscrewing the implant using a proper and known tool after a certain initial resistance has been surpassed.

In another embodiment as shown in FIG. 3b each longitudinally extending groove 19a-19c etc is applied with a certain depth in the circumferential surface 12a of the intra-osseous part 12, whereby the thread 18 is locally completely removed.

The remains of the interrupted thread 18 in this design form several rows 18a-18d etc. of thread parts, which encounter the surrounding bone as retention elements. This function guarantees a good stability of the implant in the (jaw-)bone, but also allows adjusting or removing a wrongly placed implant. The retention elements 18a-18d etc exhibit a sloping edge in the apical direction of the intra-osseous part 12 allowing an uninterrupted insertion, but preventing the removal of the implant by simply pulling. Removal is only possible by unscrewing the implant out of the implant preparation bed 13 in bone 14.

Other designs of the intra-osseous implant according to the invention are shown in FIGS. 4a-4d, 5a-5c and 6a-6b and 7, whereby the corresponding elements of the different embodiments in the Figures are indicated with the same reference numerals.

The intra-osseous part 12 exhibits an apical end side 12b, which enters the implant preparation bed 13 first and a cervical or connection end side 12c, which carries the support or connection part 15 intended for implant insertion and acting as a support or mounting area for a prosthetic device 6 (a supra-structure, e.g. crown, bridge or over denture). The surface 12a shows a thread 18, which according to the invention shows several longitudinal interruptions 19a-19c etc.

As described above, the interrupted thread parts 18a-18c etc. act like retention elements placed on rows extending in longitudinal direction along the circumferential surface 12a of the intra-osseous part 12. Due to their configuration these retention elements function like shark teeth to hook into the surrounding bone tissue 14 as the profile of the thread exhibits a shallow slope towards the apical side 12b and a steep or even rectangular slope on the cervical side 12c. See also FIGS. 3a and 3b.

Figure 4D:
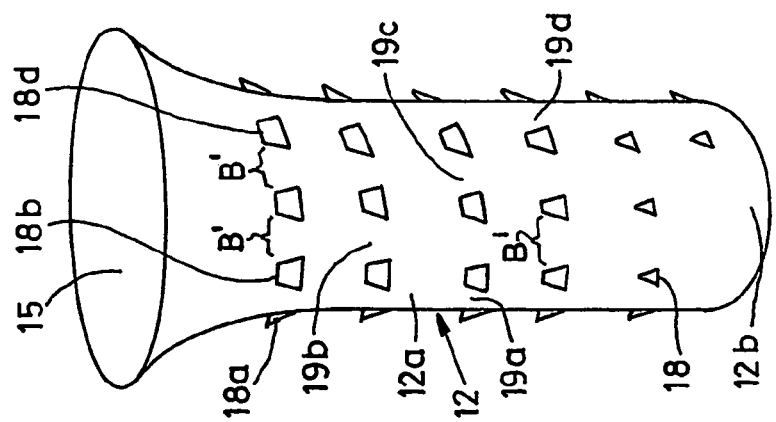
Figure 4C:
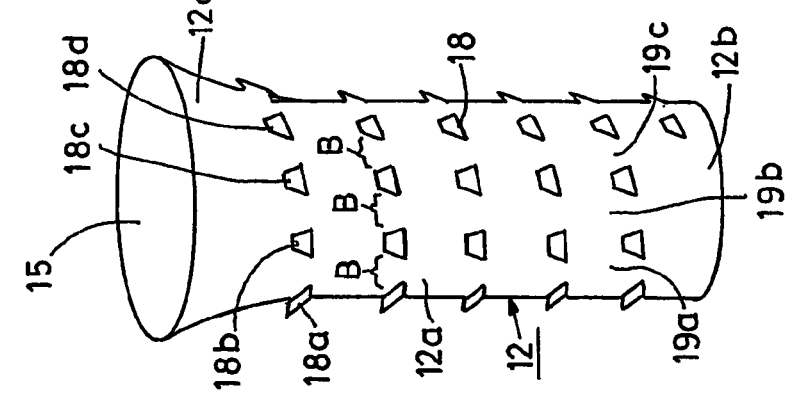
Figure 4B:
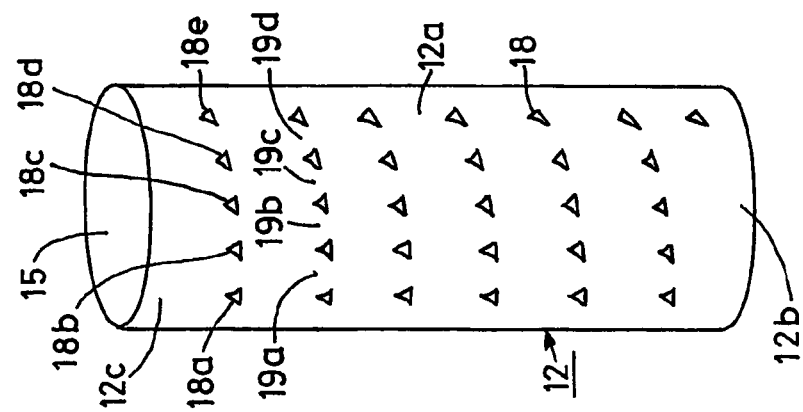
Figure 4A:
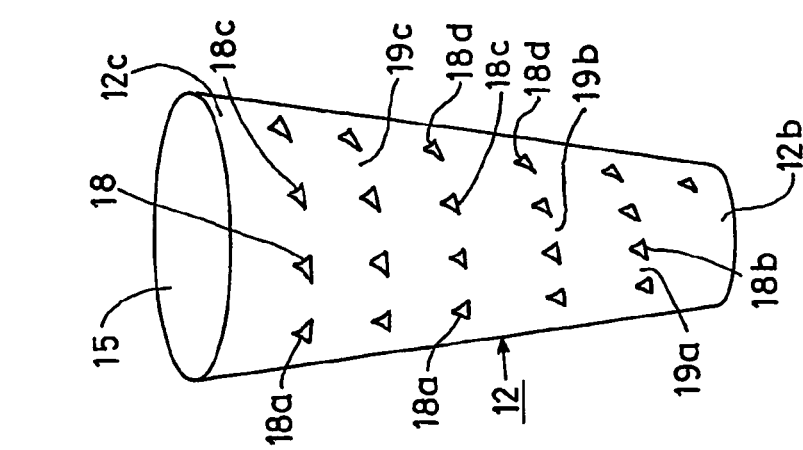

In FIG. 4a an intra-osseous implant is shown having a conical or tapered form seen in the direction of the apex 12b, while FIG. 4b shows a cross section of a cylindrical form.

FIG. 4c shows an embodiment with several grooves 19a-19c etc. extending over the entire longitudinal length of the intra-osseous part 12 having a constant width B between the interrupted rows of screw thread parts (retention elements) 18a-18c etc., whilst the width B' of grooves 19a-19c etc. increase towards the apex in the embodiment shown in FIG. 4d. In FIG. 4d the intra-osseous part 12 exhibit smaller retention elements at the apex 12b than towards the cervix 12c.

Figure 5C:
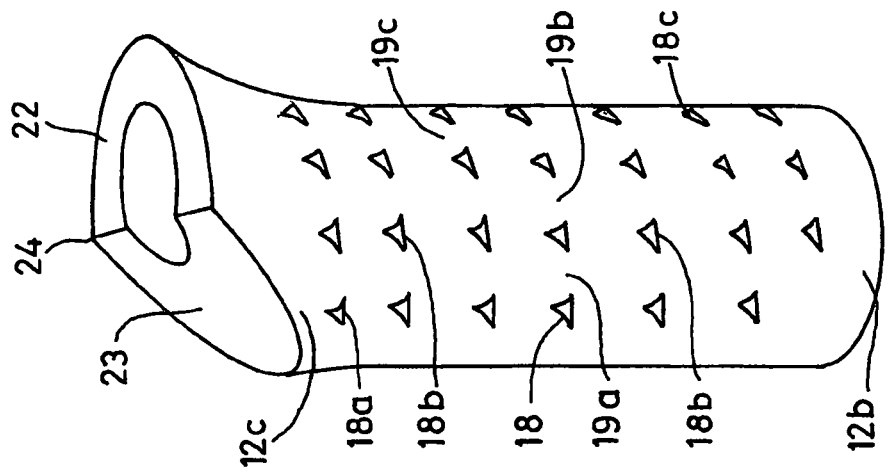
Figure 5B:
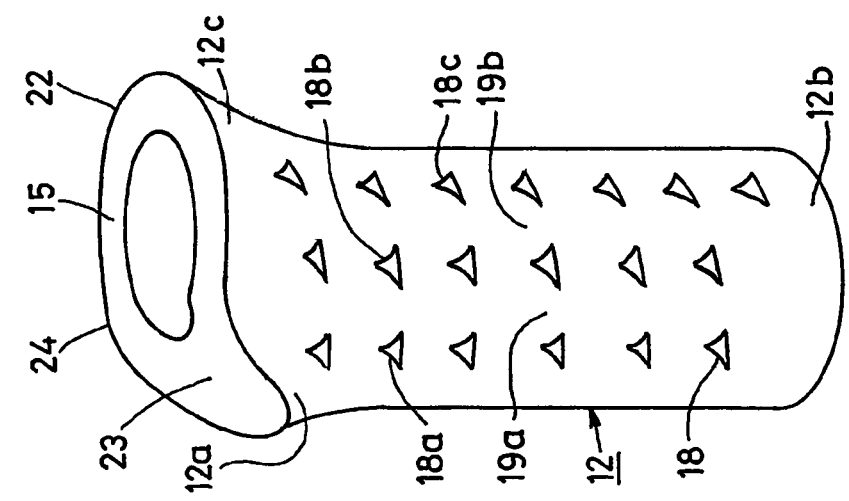
Figure 5A:
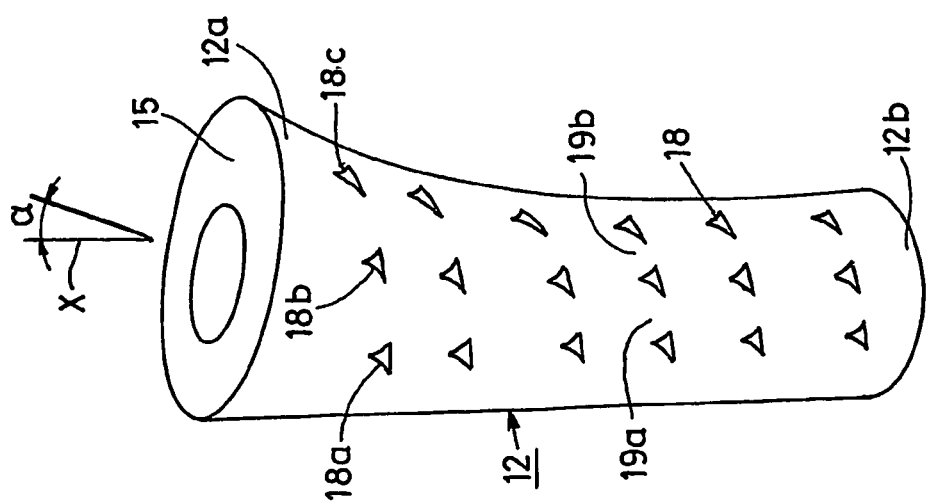

FIG. 5a-5c show further different embodiments of an intra-osseous implant according to the invention, wherein the support or connection part (cervical part) 15 of the implant is positioned under an inclined angle $\alpha$ with respect to the implant axis x of the intra-osseous part 12. The angle $\alpha$ between the axis of the support part 15 and the implant axis x of the intra-osseous part 12 may be in the range e.g. of 10°-20° and approximately 15°.

The embodiments shown in FIGS. 5b and 5c disclose at least one bevel 23 on the circumferential edge or shoulder 22 of the cervical (support) part 15 of the implant 10. In FIG. 5b the bevel 23 shows a fluent or smooth transition 24 from the shoulder 22 of the implant towards the apical side 12b, whilst in FIG. 5c the bevel 23 shows a clear and sharp transition angle 24.

As the transition 24 of the bevel 23 exhibits a convex shape in FIG. 5b, it will be apparent that also a concave transition 24 of the bevel 23 is applicable.

More specifically, the implant according to this invention is placed in such a manner that the bevel of the implant will be situated on the buccal side, so that good aesthetics can be achieved.

Figure 6B:
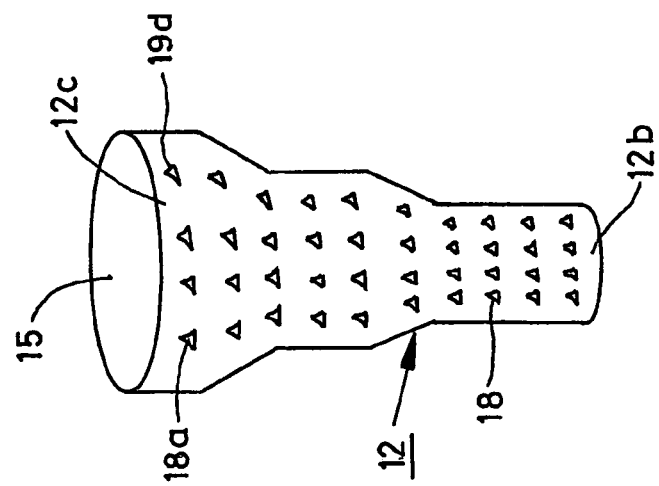
Figure 6A:
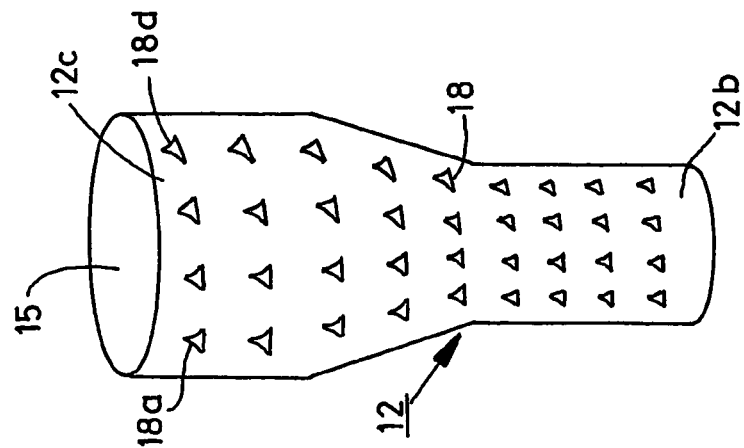

FIGS. 6a-b show combinations of embodiments of intra-osseous implants already described above and show two different combinations of a conical implant according to FIG. 4a and a cylindrical implant according to FIG. 4b. However also other combinations are possible e.g. a squar, pentagonal, hexagonal, heptagonal or octagonal design combined with a cylindrical design.

Figure 7:
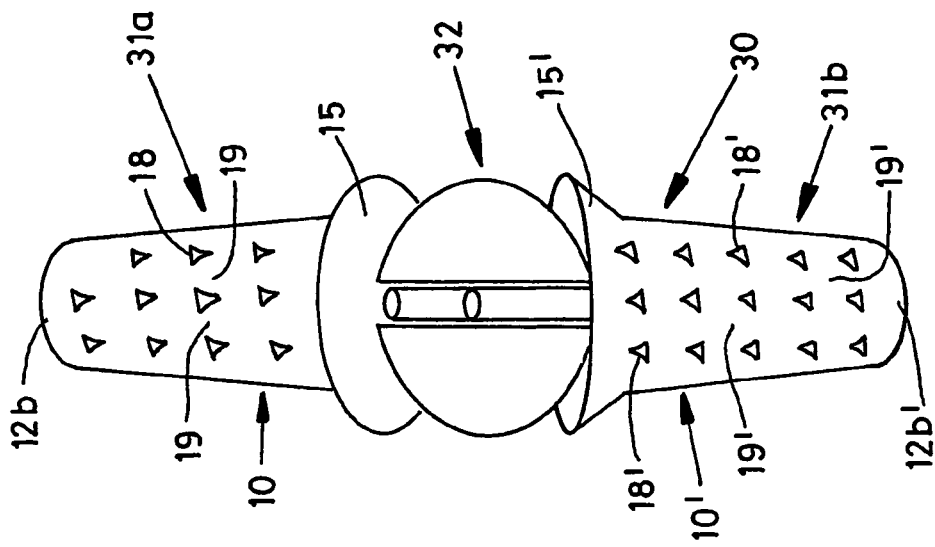

FIG. 7 shows another embodiment of the intra-osseous implant according to the invention to be used in finger or toe joint surgery. The implant 30 consists of two intra-osseous parts 31a and 31b and a joint 32. The intra-osseous parts 31a and 31b are placed in the digits of the fingers or toes or other joints. Each intra-osseous part 31a-31b is provided with a screw thread 18 resp. 18'. According to the invention the screw threads 18-18' are interrupted by several grooves 19-19'. As was described above these interrupted thread parts 18-18' act like shark teeth, hooking into the surrounding bone.

Both intra-osseous parts 31a-31b can be introduced into the finger- or toe-bone by simply using pressure or by tapping. Both intra-osseous parts 31a-31b are connected with a ballor hinge-joint 32 or other types of joints or connections, in order to restore the normal finger- or toe-joint function.

FIGS. 8a-8f show several examples of different types and variations of cross sections of the intra-osseous part 12 of the proposed implant 10 according to the invention provided with grooves 19 interrupting the screw thread 18.

Figure 8A:
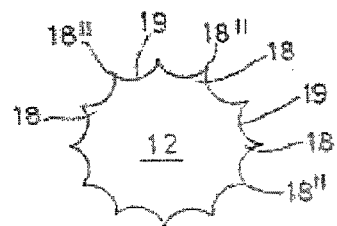
Figure 8B:
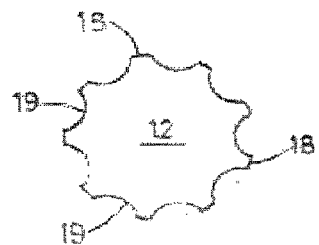
Figure 8C:
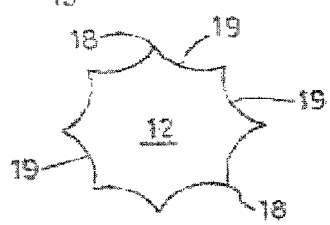

In FIG. 8a the grooves 19 show a round shape leaving sharp and pointing thread edges 18", whilst FIG. 8b shows flattened thread surfaces 18 with a polygonal cross section. FIG. 8c shows a combination of narrow 19 and wider 19' grooves with an octagonal cross section. The wide groove 19' can be used to mark the position of the bevel 23 on the support part 15. This construction makes orientation during implant placement more accurate and easy.

Figure 8D:
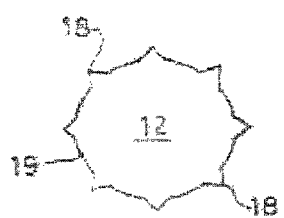
Figure 8E:
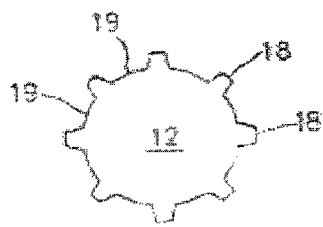
Figure 8F:
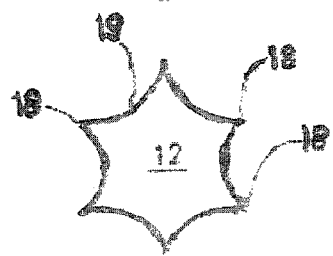

FIG. 8d shows flat grooves 19 with sharp thread edges 18, whereas FIG. 8e shows trapezoid shaped thread profiles 18 due to a specific milling operation. FIG. 8f shows grooves 19 with sharp thread surfaces 18 with a hexagonal cross section.

Figure 9:
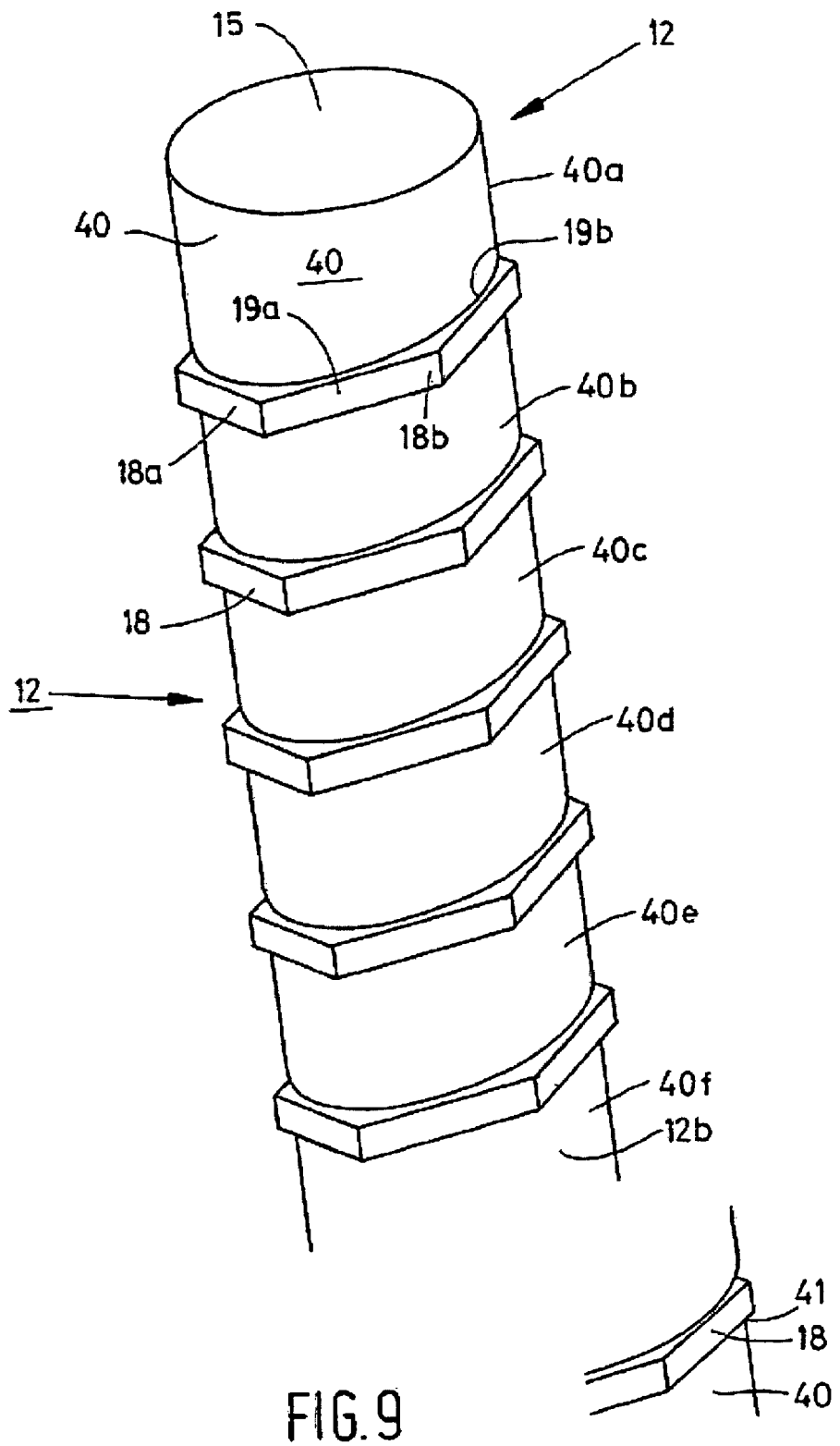

The embodiment shown in FIG. 9 exhibits an intra-osseous part 12 with a polygonal ground form, for example a hexagonal cross-section. However also an octagonal or other polygonal shapes can be used as ground form.

Using a milling or machining operation a groove 40 is applied in the circumferential surface of the intra-osseous part 12, said groove extending in one or more (helical) windings 40a-40f along the circumferential surface. Thus a screw thread 18 is created due to this milling or machining operation having flattened parts 19a-19b etc. and extending retention elements 18a-18b etc.

Preferably the surface of the flattened parts 19a-19b coincide with the surface of the groove windings 40a-40f.

The invention may also be applicable to another type of intra-osseous implant: the "screw nail" or bone tack, which in fact exhibits an interrupted screw thread as well. It can be used as a screw but also as a cylinder or as a nail (FIG. 10a-10b).

Figure 10A:
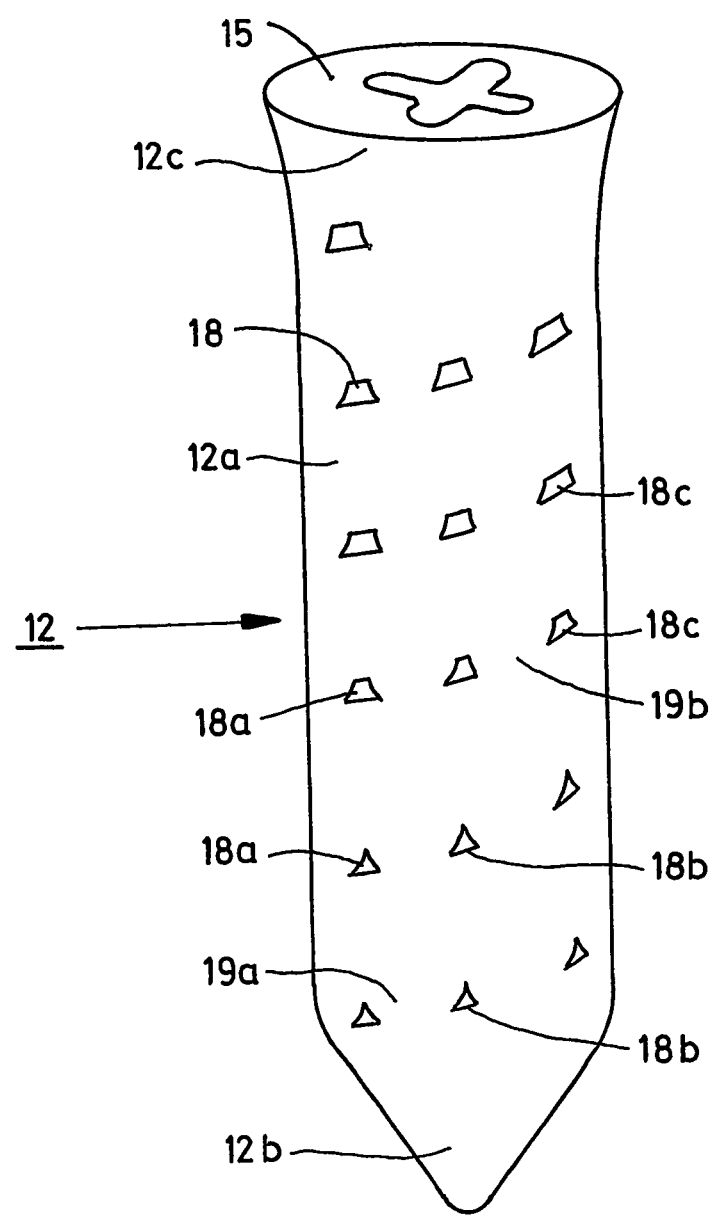
Figure 10B:
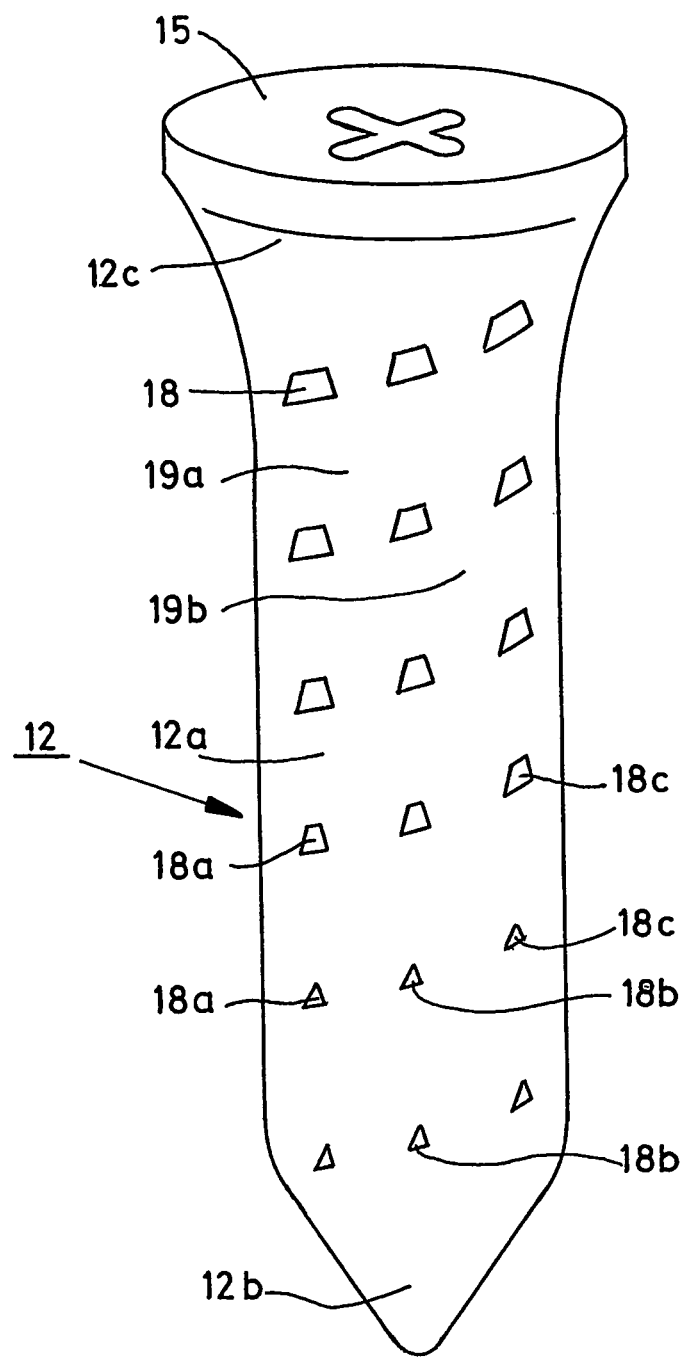

The embodiment of FIG. 10a-10b discloses an intra-osseous implant part shaped or configured as a nail. In FIG. 10b the retention elements 18 have a higher profile at the cervical end 12c than at the apical end 12b. Therefore, the depth of the grooves 19a and 19b becomes smaller towards the direction of the apical end 12b.

The invention may be or may not be combined with other structures, formations or configurations of the implant.

The invention may concern the entire length of the implant or a part of it.

The invention claimed is:

1. An intra-osseous implant for placement in bone of a human or animal body comprising at least one intra-osseous part intended for placement in bone tissue having an apical side and a cervical side and composed of a body friendly material, which part is provided on its circumferential surface with a screw thread running in the direction of and ending at the apical end; and a support part present at said cervical side of said at least one intra-osseous part intended for supporting a prosthetic element, characterized in that the intra-osseous part is provided with multiple grooves extending in longitudinal direction and over the entire length of the intra-osseous part, interrupting the screw thread into multiple interrupted screw thread parts, said multiple interrupted screw thread parts serving as retention elements allowing the placement of the implant in longitudinal direction into said bone tissue but preventing the removal of the implant in opposite longitudinal direction out of said bone, said retention elements being provided with a profile exhibiting a shallow slope towards the apical side and a steep slope on the cervical side, characterized in that the intra-osseous part has a polygonal cross section.

2. An intra-osseous implant according to claim 1, characterized in that the intra-osseous part has a hexagonal cross section.

3. An intra-osseous implant according to claim 1, characterized in that the intra-osseous part has an octagonal cross section.

4. An intra-osseous implant for placement in bone of a human or animal body comprising at least one intra-osseous part intended for placement in bone tissue having an apical side and a cervical side and composed of a body friendly material, which part is provided on its circumferential surface with a screw thread running in the direction of and ending at the apical end; and a support part present at said cervical side of said at least one intra-osseous part intended for supporting a prosthetic element, characterized in that the intra-osseous part is provided with multiple grooves extending in longitudinal direction and over the entire length of the intra-osseous part, interrupting the screw thread into multiple interrupted screw thread parts, said multiple interrupted screw thread parts serving as retention elements allowing the placement of the implant in longitudinal direction into said bone tissue but preventing the removal of the implant in opposite longitudinal direction out of said bone, said retention elements being provided with a profile exhibiting a shallow slope towards the apical side and a steep slope on the cervical side, characterized in that the width of the groove varies in the direction of the apical side of said intra-osseous part and the width of the groove widens in the direction of the apical side of said intra-osseous part.

\* \* \* \* \*